(12) United States Patent
Gallem et al.

(10) Patent No.: US 6,481,438 B1
(45) Date of Patent: Nov. 19, 2002

(54) METER

(75) Inventors: Thomas Gallem, Munich (DE); Kevin Stapleton, Boston, MA (US); Martin Knoch, Berg (DE)

(73) Assignee: PARI GmbH Spezialisten fur Effetive Inhalation, Starnberg (DE)

( * ) Notice: Subject to any disclaimer, the term of this patent is extended or adjusted under 35 U.S.C. 154(b) by 0 days.

(21) Appl. No.: 09/807,091

(22) PCT Filed: Aug. 24, 1999

(86) PCT No.: PCT/EP99/06206

§ 371 (c)(1),
(2), (4) Date: Oct. 22, 2001

(87) PCT Pub. No.: WO00/22570

PCT Pub. Date: Apr. 20, 2000

(30) Foreign Application Priority Data

Oct. 8, 1998 (DE) .......................................... 198 46 382

(51) Int. Cl.⁷ .............................. A62B 7/00; A62B 9/00; A61M 11/00; A61M 15/08; G06M 1/00
(52) U.S. Cl. ........................... 128/205.23; 128/200.14; 128/203.15; 128/203.23; 235/91 R
(58) Field of Search ...................... 128/205.23, 200.23, 128/203.15, 203.23, 203.24, 200.14; 235/91 R (56) References Cited

U.S. PATENT DOCUMENTS

| 5,349,945 | A | | 9/1994 | Wass et al. |
| 5,482,030 | A | | 1/1996 | Klein |
| 5,740,792 | A | * | 4/1998 | Ashley et al. ............... 116/299 |
| 5,988,496 | A | * | 11/1999 | Bruna ........................... 222/18 |
| 6,076,521 | A | * | 6/2000 | Lindahl et al. ......... 128/200.23 |
| 6,234,168 | B1 | * | 5/2001 | Bruna .................... 128/200.23 |
| 6,328,037 | B1 | * | 12/2001 | Scarrott et al. ......... 128/200.23 |

FOREIGN PATENT DOCUMENTS

| DE | 1 016 470 | 9/1957 |
| EP | 0 254 391 | 1/1988 |
| EP | 0 505 321 | 9/1992 |
| FR | 2 022 212 | 7/1970 |
| GB | 1 317 315 | 5/1973 |
| WO | WO86/02275 | 4/1986 |
| WO | WO93/24167 | 12/1993 |
| WO | WO95/34874 | 12/1995 |

* cited by examiner

*Primary Examiner*—William C. Doerrler
(74) *Attorney, Agent, or Firm*—Merchant & Gould, P.C.

(57) ABSTRACT

The present invention relates to a meter, especially a meter for metering aerosol devices, basically consisting of four disk units that are arranged in a parallel position and located on the same axis.

21 Claims, 6 Drawing Sheets

METER

The present invention refers to a meter, and in particular to a meter which can be used with metering aerosol devices as for instance inhalers or atomizers.

There are known various metering aerosol devices for inhalation purposes which dispense an amount of medicament or drug of an exact dose in the form of a mist or an aerosol for instance for the treatment of respiratory tract diseases. Here, above all, the reliable metering of the dispensed medicament is important so that a specific therapeutical effect for the patient can be achieved. Such metering aerosol devices are for instance the so-called MDI (metered-dose inhalers) which normally have a container for accommodating a liquid or powdery medicament, a suitably designed nozzle for atomizing and distributing the medicament, and an actuating device with a mouthpiece via which the generated medicament-containing aerosol is inhaled. In case of propellant aerosols, the actuation of the metering aerosol devices is effected for instance in such a way that the medicament container is displaced linearly with respect to the nozzle arranged in the actuating device, whereby a defined amount of the atomization material is released. A metering aerosol device of said kind is described for example in EP 0 254 391.

Metering aerosol devices usually are designed for multiple dosages. In this connection it is desirable that the number of the dispensed doses, in other words of the dispensed spraying puffs, or of the still available spraying puffs is indicated to the user in order to guarantee that the patient is informed at an early point of time of the fact that the medicament is consumed. Thereby it is avoided that a patient carries with him or her an already almost empty metering aerosol device for instance as a prophylaxis of an acute asthmatic attack.

Therefore controlled-dosage atomizers or controlled-dosage inhalers have been provided with different meters or counters. For instance in EP 0 254 391 there is described an inhaler with a flat meter which is formed on the side of an aerosol dispenser facing the patient. From EP 0 505 321 there is known a reusable inhaler with a resettable meter which is incremented when the first relative position of storage chamber and metering pin is reached. The meter disclosed in GB 1 317 315 has a plurality of annular elements which cooperate mechanically in order to indicate at an indicator ring the dosages still available. Further medicament dispensers with a mechanical meter are disclosed for instance in WO 86/02275 and WO 93/24167.

The known meters for metering devices, however, have either a complex, unmanageable structure or require rather considerable modifications of an already existing metering aerosol device to enable the use thereof together with a meter. But such a modification of an already existing metering device is disadvantageous in that after-wards said device has once again to be subjected to an official approval procedure and the tests involved therewith regarding the medical applicability. This, however, usually is a tedious and expensive process and therefore is undesirable.

Moreover, the known meters are expensive and therefore are not suitable for the mass production of a product which, otherwise, can be manufactured at low costs.

Consequently, proceeding from prior art, the object of the present invention is to develop a meter with small dimensions which has a simple and therefore low-cost design and which can be used with different inhalers for counting the dosages without substantial modifications having to be carried out at the inhalers.

This object is solved according to the invention by a meter comprising four disk units which are arranged in parallel to each other, the centers of which are located on an axis extending perpendicularly to the planes of the four disk units, and a first disk unit of which has first receiving means for taking up a force effecting a rotation of the first disk unit around the axis and first transmission means for the transmission of the motion of rotation onto a second disk unit which includes second receiving means for taking up a force being transmitted by the first transmission means and effecting a rotation of the second disk unit around the axis and second transmission means for transmitting the rotation onto a fourth disk unit which includes third receiving means for taking up a force transmitted through the second transmission means and effecting a rotation of the fourth disk unit around the axis.

Advantageously, the third disk unit defines a fixed position with respect to which the first, second and fourth disk units are mounted rotatably.

In one embodiment the first receiving means of the first disk unit are an external toothing. Furthermore, the first transmission means and the second receiving means are realized in the form of a fixed connection between the first and the second disk unit.

In said embodiment the second transmission means is realized in the form of a spring cam which is arranged elastically at the outer contour of the second disk unit, and the third receiving means is realized in the form of an internal toothing at the fourth disk unit.

To the end that the spring cam comes into engagement with the internal toothing of the fourth disk unit, at the outer contour of the third disk unit at least one projecting part is provided which in a predetermined rotational position of the second disk unit relative to the third disk unit deviates the spring cam in radial direction.

In an advantageous development, the spring cam is wedge-shaped, and the width of the spring cam is larger than the thickness of the second disk unit so that the spring cam projects over the second disk unit in the direction of the axis.

In order to avoid an unintentional reset of the meter, the fourth disk unit has a second toothing circularly formed around the central point of the fourth disk unit, and the third disk unit has a plurality of snap-in toothings for the engagement into the second toothing of the fourth disk unit.

Advantageously, the radius of the second disk unit is larger than the radius of the first disk unit, the radius of the third disk unit is larger than the radius of the first disk unit and smaller than the radius of the second disk unit, and the radius of the fourth disk unit is larger than the radius of the first, the second and the third disk units.

For mounting the four disk units, a bearing pin is provided in a preferred embodiment which has a first section for slidably mounting the first and second disk unit and a second section for slidably mounting the fourth disk unit, and at which the third disk unit is secured between the first and second section.

The bearing pin is used preferably also for securing the meter at an object, for instance an inhaler or metering aerosol generator, and for this purpose the bearing pin has a third section which, on the side of the first disk unit, extends out of the meter.

In order to prevent an unintended reset, the second disk unit has an internal toothing. As counterparts, at the bearing pin there are arranged preferably L-shaped locking elements which interact with the internal toothing of the second disk unit.

In a particularly advantageous development, the meter comprises four disk units which are arranged in parallel to each other, the center points of which are located on an axis extending perpendicularly to the planes of the four disk units. A first disk unit has first receiving means for taking up a force effecting a rotation of the first disk unit around the axis and first transmission means for transmitting the rotation onto a second disk unit. The second disk unit has second receiving means for taking up a force transmitted by the first transmission means and effecting a rotational movement of the second disk unit around the axis. Furthermore, the second disk unit has a spring cam which is arranged elastically at the outer contour of the second disk unit for the transmission of the rotation onto a fourth disk unit which in turn has an internal toothing for taking up a force transmitted through the spring cam and effecting a rotation of the fourth disk unit around the axis. Here, at the outer contour of a third disk unit, there is provided at least one projecting part which in a predetermined rotational position of the second disk unit relative to the third disk unit deviates the spring cam in radial direction so that the spring cam comes into engagement with the internal toothing of the fourth disk unit, wherein at least one tooth of the internal toothing of the fourth disk unit is filled up in order to lead to a locking effect. The advantages of said development will be described in the description of the embodiments.

In an alternative development which, however, is also especially advantageous, the meter includes four disk units which are arranged in parallel to each other, the centers of which are located on an axis extending perpendicularly to the planes of the four disk units. A first disk unit has first receiving means for taking up a force effecting a rotation of the first disk unit around the axis and first transmission means for transmitting the rotation onto a second disk unit. The second disk unit has second receiving means for taking up a force transmitted by the first transmission means and effecting a rotation of the second disk unit around the axis. Furthermore, the second disk unit has a spring cam which is arranged elastically at the outer contour of the second disk unit for the transmission of the rotation onto a fourth disk unit which in turn has an internal toothing for taking up a force transmitted by the spring cam and effecting a rotation of the fourth disk unit around the axis. Here at the outer contour of a third disk unit there is provided at least one projecting part which in a predetermined rotational position of the second disk unit relative to the third disk unit deviates the spring cam in radial direction so that the spring cam comes into engagement with the internal toothing of the fourth disk unit, wherein at least one tooth of the internal toothing of the fourth disk unit is removed in order to suppress an engagement of the spring cam. The advantages of said development will be described in the description of the embodiments.

The inventive meter of the above-described kind is especially used in inhalers, atomizers or similar metering aerosol devices. Toward this end, the meter is of a special design and, due to its simple design which is therefore favorable as regards costs, is excellently suitable for said application. In particular the fastening by means of the end of the bearing pin projecting out of the meter contributes to the unproblematic use in any metering aerosol device.

This is an important advantage of the invention, as the inventive meter can be used with different inhalers, atomizers or similar metering aerosol devices without the known devices having to be essentially modified. This has the advantage that the metering aerosol devices have not once again to be subjected to tedious and costly tests regarding the clinical applicability and to approval procedures.

Furthermore, the inventive meter has small dimensions and, therefore, a handy system can be formed in a space-saving manner out of the meter together with the metering device.

Further features and advantages of the present invention result from the following description of a preferred embodiment which is described in connection with the accompanying drawings, wherein.

Figure 1:
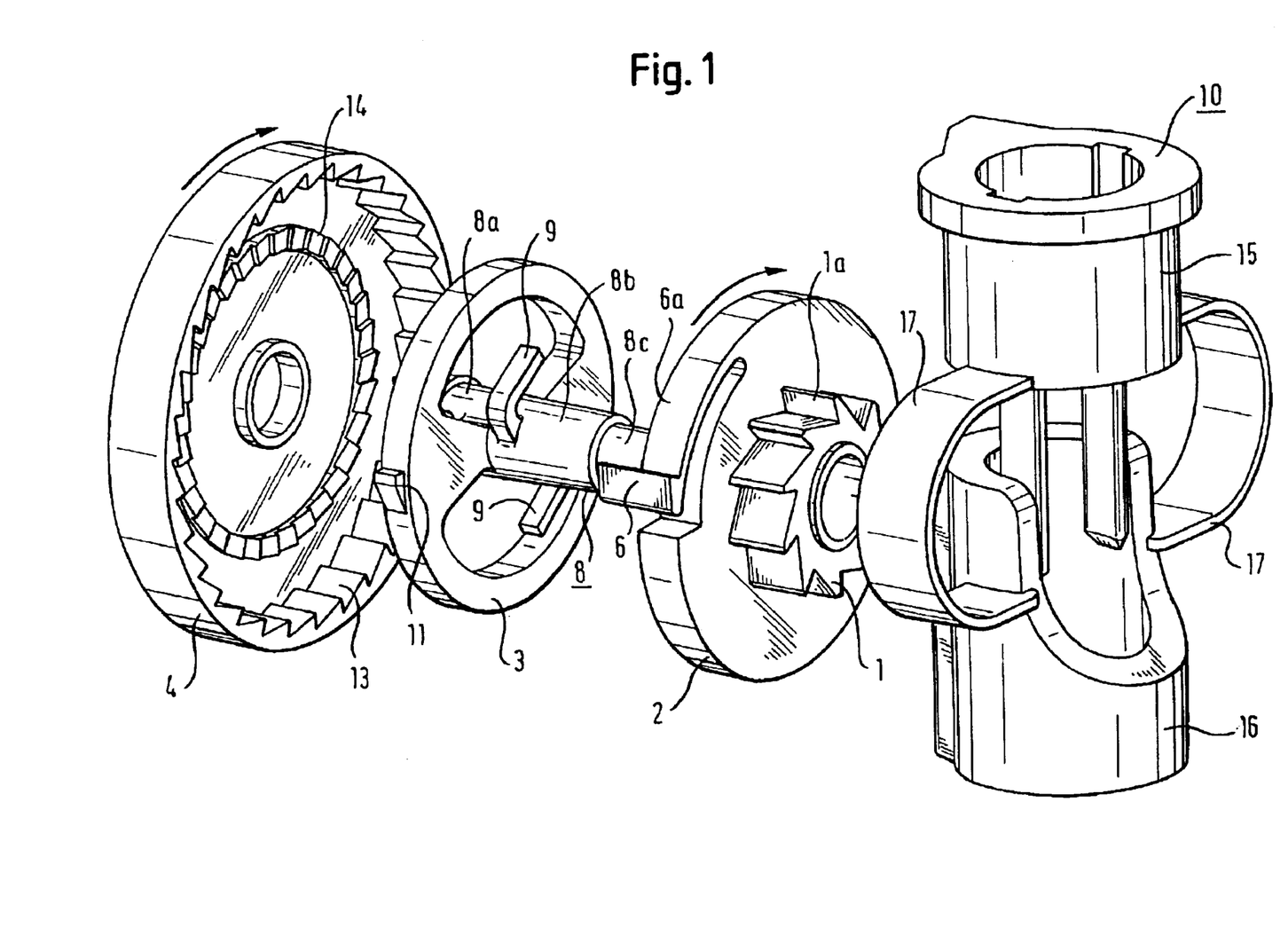
FIG. 1 shows an exploded view of the inventive meter which is connected with an actuating device of a metering aerosol generator.
Figure 2:
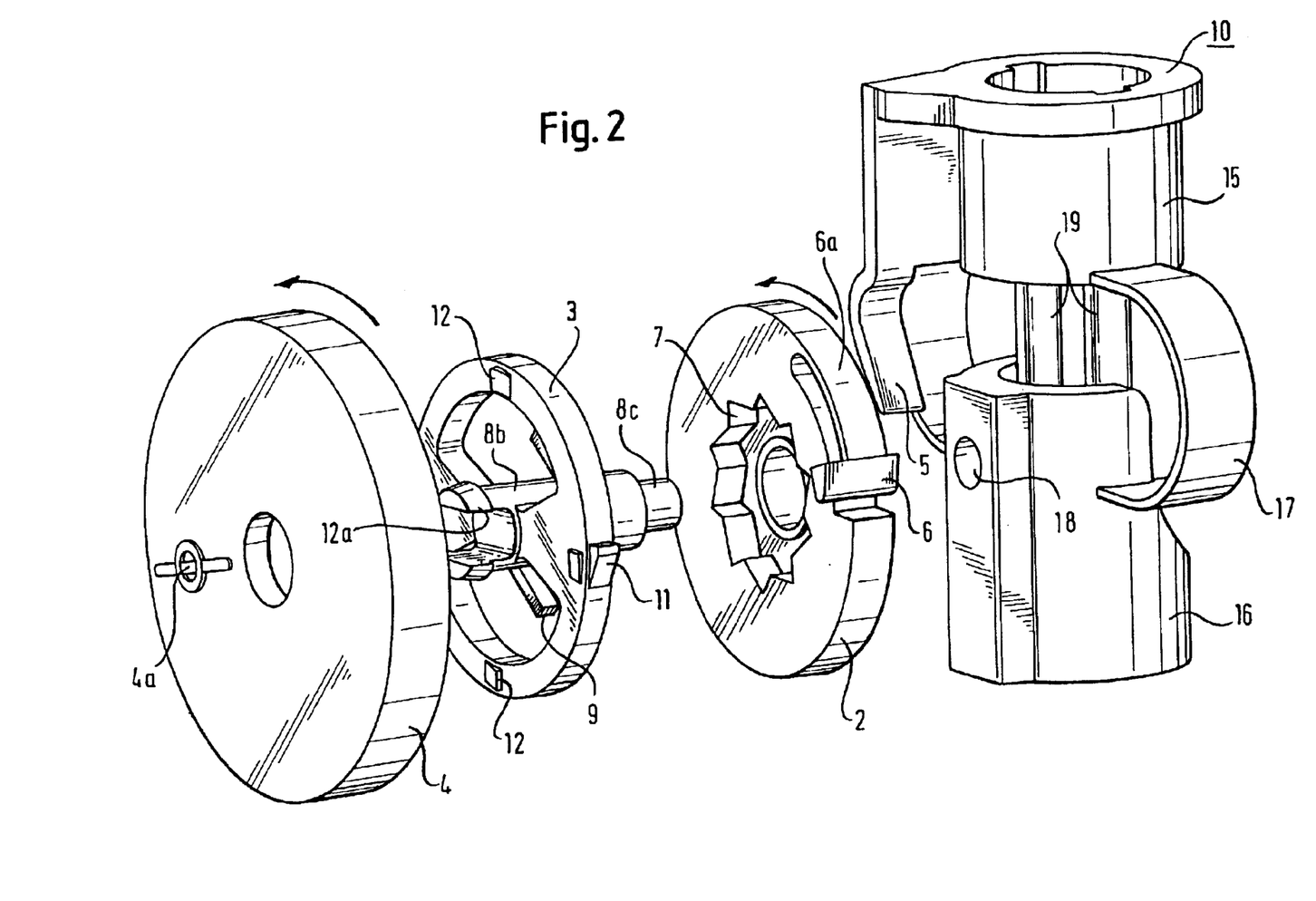
FIG. 2 shows an exploded view of the meter shown in FIG. 1, seen from a viewing direction different to that in FIG. 1.

The individual components of the inventive meter will be described in the following with reference to FIGS. 1 and 2. FIGS. 1 and 2 each show exploded views of the meter viewed from two different viewing directions.

Basically, the meter has four disk units 1, 2, 3 and 4 which are arranged in parallel to each other. The centers of the disk units 1, 2, 3 and 4 lie on an axis extending perpendicularly to the disk units and, as will be described in more detail in the following, are connected with an actuating device 10 of a metering aerosol generator (not shown) by means of a bearing pin 8. The first, second and fourth disk units 1, 2 and 4 are arranged rotatably relative to the actuating device 10. The third disk unit 3 has a fixed position relative to the actuating device 10 and thus also relative to the other disk units.

The first disk unit 1 has a means for taking up a force which effects a rotation of the first disk unit; said means is an external toothing 1a into which an actuating arm 5 attached at the actuating device 10 engages (see FIGS. 1 and 2). The first disk unit 1 has a smaller radius than the second disk unit 2 and is fixedly connected therewith. By said fixed connection the transmission of the rotation from the first disk unit 1 onto the second disk unit 2 is realized. But at the two disk units there can also be provided other means for the transmission of the rotation and for the taking-up of the force effecting a rotation.

In order to transmit the motion of rotation to a fourth disk unit 4, as a transmission means a wedge-shaped cam 6 is arranged at the outer circumference of the second disk unit 2, said cam 6 being connected to the second disk unit 2 via a spring element 6a and being called a spring cam in the following. The spring element 6a forms substantially the outer contour of the second disk unit 2, but has a freely swinging end. At the freely swinging end the wedge-shaped spring cam 6 is arranged in such a way that in the rest position it projects over the outer contour of the second disk unit 2 in radial direction. The geometry of the spring cam is chosen such that the cam or nose engages the internal toothing 13 of the fourth disk unit 4 in case of a deviation in radial direction.

For this purpose, the wedge-shaped spring cam 6 is arranged such that the sharp and the blunt edge are orientated normal to the plane of the second disk unit 2. Furthermore, the spring cam 6 has a width which is larger than the thickness of the second disk unit 2 so that the spring cam 6 extends like a pin in parallel to the axis of the disk units in the direction towards the third and fourth disk unit 3 and 4.

In interaction with the other elements of the meter which will be explained in more detail particularly with reference to FIG. 3 and 4, the spring cam 6 projecting like a pin in the direction of the third and fourth disk units can come into engagement with a first toothing 13 of the fourth disk unit 4 (see FIG. 2).

The side of the second disk unit 2 pointing towards the third and fourth disk unit has an internal toothing 7 which is arranged symmetrically around the axis of the disk units. The internal toothing 7, which is seen in FIG. 2 but not in FIG. 1, has the same number of teeth as the external toothing of disk unit 1. In the embodiment represented in FIG. 1 and FIG. 2, the number of teeth is ten so that together with a first internal toothing 13 of the fourth disk unit 4 with 24 teeth, a total of 240 discrete steps of counting can be realized. But also other values can be easily used.

The radius of the third disk unit 3 is identical to or preferably slightly smaller than the radius of the second disk unit 2. Furthermore, at the outer circumference of the third disk unit 3 there is arranged a wedge-shaped shoulder 11 which is used for actuating the spring cam 6 arranged at the second disk unit 2 which will be explained in more detail in the following. When a further shoulder is arranged, the transmission ratio is changed. The third disk unit 3 is fixedly connected with a bearing pin 8.

With respect to the third disk unit 3, the bearing pin 8 has three different sections, namely section 8a pointing towards the fourth disk unit 4, and sections 8b and 8c pointing towards the first and second disk unit. The diameter of the bearing pin section 8b is identical to the diameter of section 8a, and the diameter of section 8c is reduced compared therewith. The bearing pin 8 is used for attaching the third disk unit 3 at the actuating device 10 such that the disk unit 3 is fixed with regard to a rotation therewith, and for the rotatable mounting of the first, second and fourth disk units 1, 2 and 4. For this purpose, the bearing pin section with the smaller radius 8c is inserted into a corresponding opening 18 of the actuating device 10 and secured such that the position of the third disk unit 3 relative to the actuating device 10 is fixed. The openings provided in the first and second disk units 1 and 2 are coordinated with the diameter of the bearing pin section 8b such that the first and second disk units 1 and 2 are slidably rotatable on the bearing pin section 8b. It is to be noted that the diameters of the sections 8a, 8b and 8c are not restricted to the ratio represented in FIG. 1 or FIG. 2. It is important that the respective openings of the disk units and the diameters of the bearing pin sections are coordinated with each other.

Furthermore, at the bearing pin 8 there are arranged two L-shaped locking elements 9 which are arranged at the outer circumference of the bearing pin section 8b and which engage into the internal toothing 7 of the second disk unit 2. The opening of the fourth disk unit 4 is coordinated with the diameter of the bearing pin section 8a in such a way that the fourth disk unit 4 is slidably rotatable on the bearing pin section 8a. At the section 8a there are also arranged symmetrically two snap hooks 12a pointing towards the fourth disk unit 4, said snap hooks 12a being used for the axial fixing of the disk unit 4.

On the side of the third disk unit 3 pointing towards the fourth disk unit 4 there is arranged a snap-in toothing 12 which can be seen in FIG. 2. In the embodiment represented in FIG. 2 the snap-in toothing 12 consists of four elements which are spaced apart from each other by 90°. The snap-in toothing can, however, also consist of one or of several elements which are arranged centrically around the axis of the bearing pin 8. Said snap-in toothing 12 comes into engagement with a second toothing 14 of the fourth disk unit 4 and is substantially used for securing the rotational position of the disk unit 4.

The design of the fourth disk unit 4 can be inferred in particular from FIG. 1. The side of the fourth disk unit 4 pointing towards the other disk units has a first toothing 13 which is arranged at the inside of the circumference, and a second toothing 14 circularly arranged around the central point of the fourth disk unit 4. The radius of the second toothing 14 is coordinated with the position of the elements of the snap-in toothing 12 provided at the third disk unit 3.

In the assembled state, the first and second disk units 1 and 2 are arranged on the bearing pin section 8b; here the L-shaped locking elements 9 rest in the recess of the internal toothing 7 of the second disk unit 2. The spring cam 6 projects over the outer contour of the third disk unit 3. The fourth disk unit 4 is arranged on the bearing pin section 8a and, due to its cap-like form, accommodates the third disk unit 3; here the spring cam 6 lies between the outer contour of the third disk unit 3 and the first internal toothing of the fourth disk unit 4.

In the following the functioning of the inventive meter is explained. Since an actuating arm 5 engages into the external toothing of the first disk unit 1, as is shown in FIG. 2, by an actuation of the arm 5, which will be described in more detail in the following by reference to FIG. 5, the first disk unit 1 is rotated in the direction of the arrow indicated in FIGS. 1 and 2. In this connection the second disk unit 2 is rotated therewith, as the first and second disk units 1 and 2 are fixedly connected with each other. Here the first and second disk units 1 and 2 slide along the bearing pin section 8b. In contrast thereto, the third disk unit 3 is fixedly connected to the actuating device 10 via the bearing pin 8 so that the position of the third disk unit 3 relative to the actuating device 10 remains unchanged at any time. Simultaneously, the L-shaped locking elements 9 arranged at the bearing pin section 8b are in engagement with the internal toothing 7 of the disk unit 2; but the design of the locking elements 9 and of the internal toothing 7 allows a rotation of the first and second disk units 1 and 2 in the direction shown in FIGS. 1 and 2. When the first and second disk units 1 and 2 are rotated in the direction of the arrow, the locking elements 9 lock into the respective following toothing of the internal toothing 7. When the arm 5 is operated once again, the disk units 1 and 2 rotate on by exactly one tooth and the locking arm engages the next tooth. By such an engagement of the locking elements 9 into the internal toothing 7 it is guaranteed that the first disk unit and thus also the second disk unit do not rotate backwards when the actuating arm 5 is released out of engagement with the disk unit 1 which is shaped like a toothed wheel, i.e. that they do not move back contrary to the direction of the arrow.

When the first and second disk unit 1 and 2 are rotated in the direction of the arrow as indicated in FIGS. 1 and 2, the spring cam 6 arranged at the second disk unit 2 runs along the outer contour of the third disk unit 3. When proceeding from a toothed gear with ten teeth and when the arm 5 is actuated ten times, the spring cam 6 moves over an angle of 360°, i.e. the spring cam makes one complete rotation and reaches again its starting position. As long as the spring cam 6 is not influenced by the shoulder 11 of the third disk unit 3, the spring cam 6 does not engage into the first toothing 13 arranged at the inner circumferential side of the fourth disk unit 4. Only when the shoulder 11 raises the spring cam 6 in radial direction, the spring cam 6 comes into engagement with the first internal toothing of the fourth disk unit 4 and effects a rotation of the fourth disk unit around a rotational position.

The step-by-step rotation of the disk unit 2 relative to the third disk unit 3 as well as the engagement of the spring cam 6 of the second disk unit 2 into the internal toothing 13 of the fourth disk unit 4 are described in detail in the following with reference to FIGS. 3 and 4. FIGS. 3 and 4 show schematical cross-sectional views which explain in particular the cooperation of the second and third disk units 2 and 3 in a more detailed manner. In FIGS. 3 and 4 the disk units 2 and 3 are represented viewed from the direction of view shown in FIG. 2. For reasons of a better general survey, the third disk unit 3 is indicated in both representations only in broken lines. FIG. 3 shows the above-mentioned starting position or resting position of the second disk unit 2 relative to the third disk unit 3 fixedly connected with the actuating device 10. In said position the locking element 9 is locked in the first tooth 7-1 of the internal toothing 7. By actuation of the actuating arm 5 which engages into the toothed wheel-shaped first disk unit 1 (not shown in FIG. 3), the disk unit 2 is rotated step-by step, i.e. tooth by tooth, in the direction of the arrow as indicated in FIG. 3. Here, starting from the first inner tooth 7-1, the locking element 9 engages the teeth 7-2 through 7-9 in ascending order. During the rotation of the first and second disk unit 1 and 2 initiated by the actuating arm 5, the spring cam 6 runs along the circumference of the third disk unit 3 represented by a broken line in FIG. 3 without any deviation of the spring cam 6. In this case the spring cam 6 does not engage into the first toothing 13 of the fourth disk unit 4.

Figure 3:
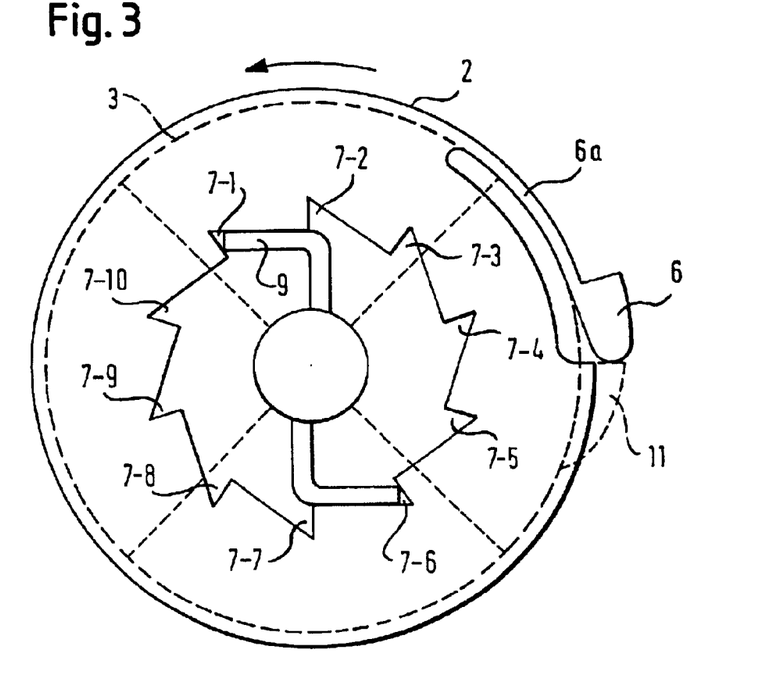
FIG. 3 shows a schematic cross-sectional view of a starting position or resting position of the second and third disk units for explaining the cooperation between the second and third disk units.
Figure 4:
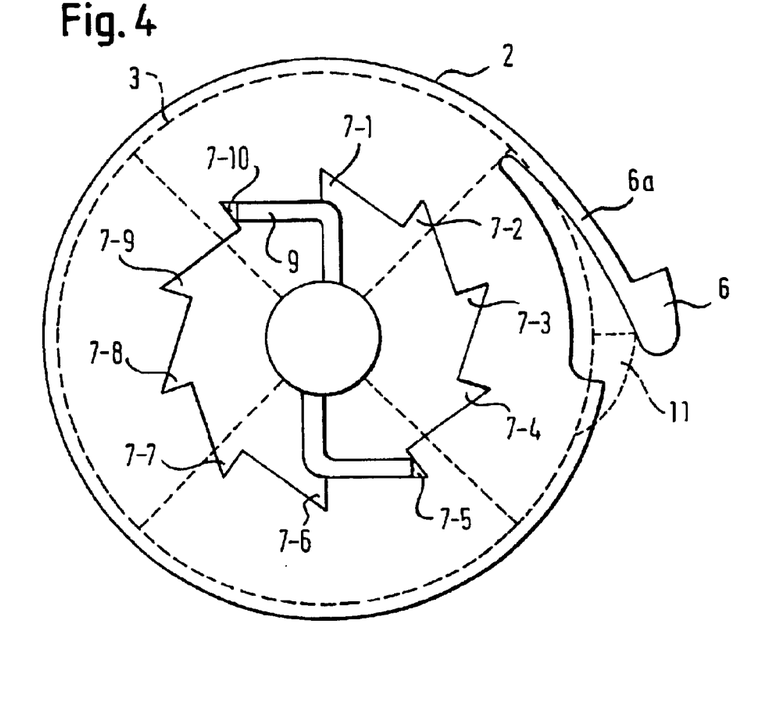
FIG. 4 shows a schematic cross-sectional view analogous to FIG. 3 which illustrates the second and third disk units in a position in which the second disk unit is caused by the third disk unit to cooperate with the fourth disk unit.

When the actuating arm 5 has been actuated so often that the locking element 9 locks into the tooth 7-10 of the internal toothing 7, i.e. when, proceeding from the starting position shown in FIG. 3, the actuating arm 5 has been actuated for the ninth time, then the spring cam 6 is in contact with the shoulder 11. The effect thereof is that the spring cam 6, as is shown in FIG. 4, is deviated in radial direction. In other words, the spring cam 6 is actuated in this position by the shoulder 11 and the spring cam 6 engages the toothing 13 at the inner circumference and rotates the fourth disk unit 4 forward by one tooth of the first toothing 13 in the direction of the arrow.

During this rotation of the fourth disk unit 4 effected by the cooperation of the shoulder 11 and the spring cam 6, the second toothing 14 arranged at the inside of the fourth disk unit 4 pointing towards the first, the second and the third disk unit comes into engagement with the snap-in toothing 12. The snap-in toothing 12 and the second toothing 14 of the fourth disk unit 4 here serve to secure the fourth disk unit 4 against rotation, and by the snap hooks 12a there is guaranteed an axial fixation of the fourth disk unit 4.

Figure 5A:
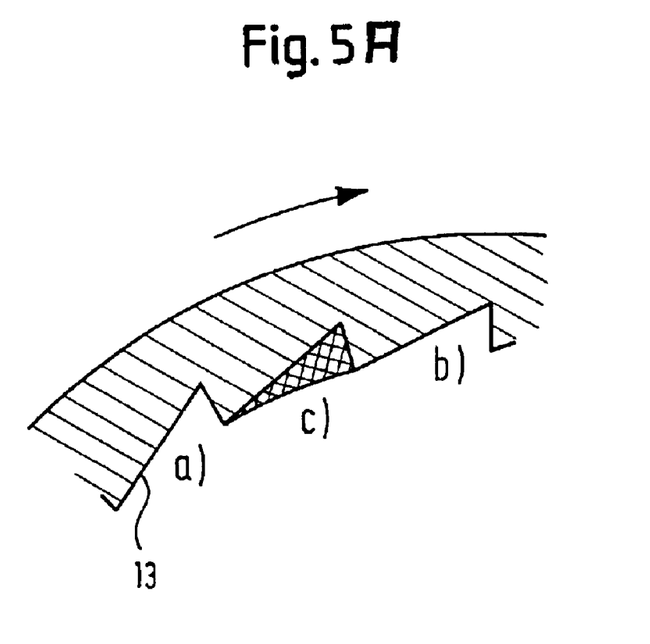
FIGS. 5A and 5B each show a detail of the internal toothing of the fourth disk unit with a counting value limitation.

When a locking is desired after a single passage of all teeth of the disk unit 4, this can be achieved in that, instead of the 24 teeth as described above, only 23 teeth are formed and a tooth gap is left free. Said kind of locking is represented in FIG. 5A which shows a detail of the internal toothing 13 of the fourth disk unit 4. The rotation of the fourth disk unit 4 is carried out in the directions of the arrow, and the positions a) and b) indicate the starting position and the final position. The tooth located therebetween (position c)) is not formed whereby the locking effect is obtained.

Figure 5B:
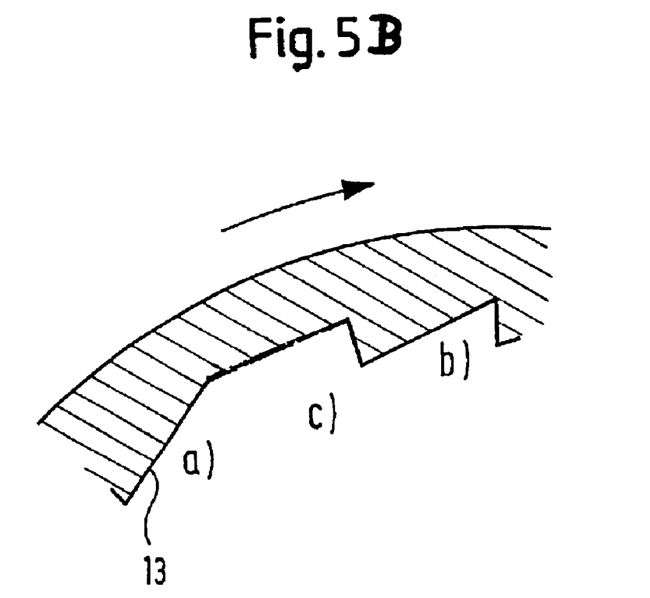

In FIG. 5B there is shown another development of the fourth disk unit 4 by which it is prevented that the fourth disk unit 4 continues to rotate after the reaching of a maximum counting value. In this embodiment, at the location c) a tooth of the internal toothing has been left out so that not even in the position deviated by the shoulder 11 the spring cam 6 comes into engagement with the internal toothing 13 of the fourth disk unit 4. This means that after an almost complete revolution of the fourth disk unit 4 a further rotation is prevented.

The development according to FIG. 5B is advantageous in that, on the one hand, a shifting onward of the fourth disk unit 4 is avoided but that, on the other hand, a further movement of the actuating device and thus an actuation of the atomizer (MDI) is not impaired. This means for the user that it is reliably indicated to him or her when the maximum number of spraying puffs has been reached but that the user is not prevented from further using the atomizer (MDI). With regard to the diseases to be treated by means of atomizers of the kind being under discussion here (MDI), for instance asthmatic attacks, this is an important advantage, as by the second development according to FIG. 5B no locking of the entire system is effected which hinders the user from the output of a—perhaps life-saving—spraying puff. By the inventive design the further use thereof is possible.

It really is to be expected that not only in emergency situations as described above, but also during normal use the user acts upon the device with such an enormous strength that the mechanism which actually is to effect a locking does not withstand the affecting forces and is at least partially destroyed. The parts coming off in this connection form fragments in a moment in which the user wants to deeply inhale the generated aerosol. Thereby particles of the destroyed meter can be inspired therewith. Also this is effectively avoided by the development according to FIG. 5B, because a further use of the device is possible, without the meter, however, being shifted onwards visibly.

In the following actuation of the first or second disk unit by the actuating arm 5, the second disk unit 2 once again resumes the starting position represented in FIG. 3, and the movement of the spring cam 6 described above with reference to FIG. 3 is once again passed through, without the spring cam 6 coming into engagement with the first toothing 13 of the fourth disk unit 4. Only when the locking element once again locks into the tooth 7-10 of the internal toothing 7, the spring cam 6 is once again deviated by the shoulder 11 so that it comes again into engagement with the internal toothing 13 and thereupon rotates the fourth disk unit 4 forward by one tooth of the first internal toothing 13. In this way, when the first disk unit has ten teeth, the fourth disk unit 4 is rotated further by exactly one tooth of the first toothing 13 each time after ten actuations of the actuating arm 5. When the first internal toothing 13 of the fourth disk unit 4 has for instance 24 teeth, the maximum number of counting positions in this case amounts to 240, i.e. when the fourth disk unit 4 is rotated by 360°, 240 actuations of the actuating arm 5 are counted. The second toothing 14 of the fourth disk unit 4 has the same number of teeth as the first internal toothing 13.

It is to be noted that the number of teeth of the first and second toothings 13 and 14 can be adapted correspondingly to the desired transmission. A 30-teeth first or second toothing 13 or 14 thus can be used for a counting of up to 300 actuations. The transmission ratio of the inventive meter or the number of countings, however, can also be varied by arranging another shoulder or several shoulders at the outer edge of the third disk unit 3. This enables in particular an uncomplicated and rapid adaptation of the inventive meter to a desired transmission ratio.

The fourth disk unit 4 can be designed in the form of an indicating disk in order to indicate the countings correspondingly. This can be achieved for instance by an imprinted pointer or a color marking on the front side as well as on the edge of the fourth disk unit 4. In the embodiment represented in FIG. 2 there is indicated a pointer indicating element 4a. In accordance with the rotational position of the fourth disk unit 4, the pointer indicates the number of actuations.

The above described meter can be used together with different actuating devices, as far as the movement of the actuating device is transmitted by means of an actuating arm onto the meter. In the following a particularly advantageous actuating device 10 according to the invention is explained as an example in detail.

The actuating device 10 represented in FIGS. 1 and 2 includes a cylindrical sleeve 15 and a cylindrical lower part 16. At the outside of sleeve 15 there is arranged an actuating arm 5. The sleeve 15 and the lower part 16 are connected to each other via an arcuate spring 17. When the spring 17 is actuated, i.e. when the sleeve 15 and the lower part 16 are pressed together in axial direction, a linear movement of the sleeve 15 relative to the lower part 16 is guaranteed by suitable guiding elements 19 which are arranged at the sleeve 15 in a manner pointing towards the lower part 16. Therein the inner circumferential side of the sleeve 15 slides along the outside of the guiding elements 19. It is essential that a straight-lined movement of the sleeve 15 and thus also a straight-lined movement of the actuating arm 5 are guaranteed when the actuating device 10 is pressed together, and a reliable engagement of the actuating arm 5 into the toothed wheel-shaped first disk unit 1 is obtained.

Figure 6:
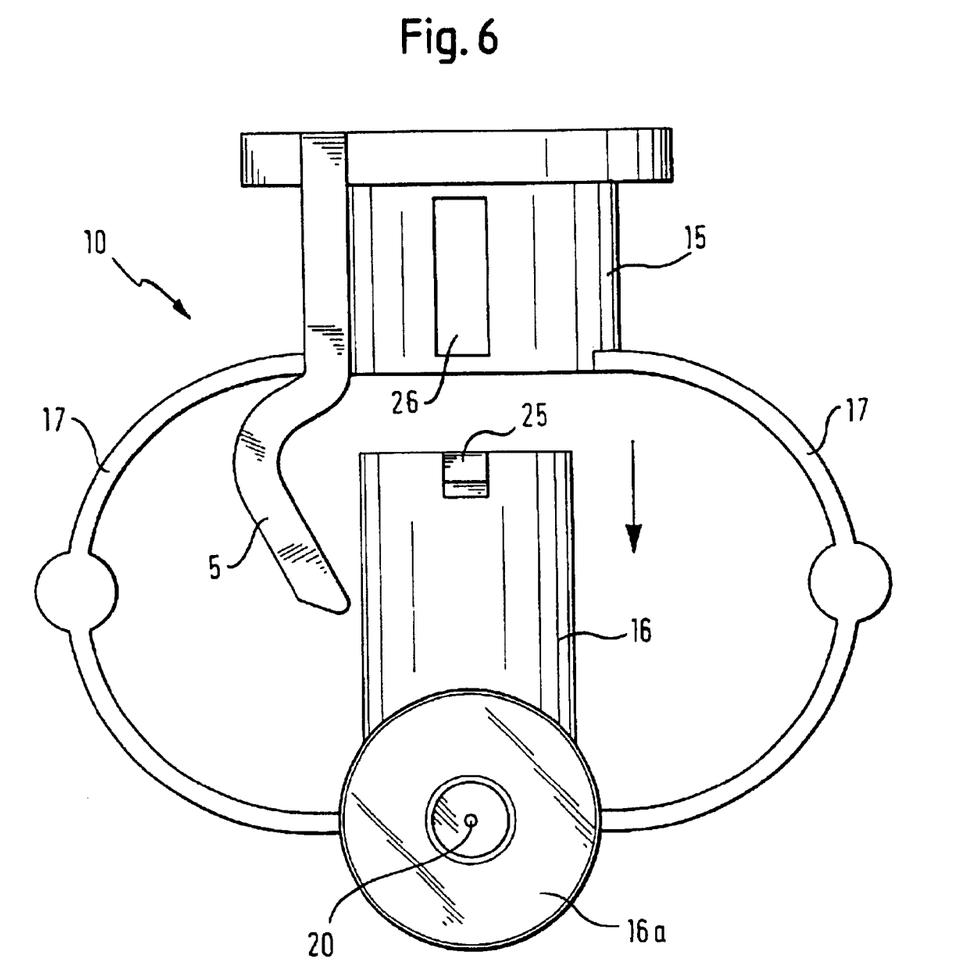
FIG. 6 shows a side view of an alternative development of the actuating device represented in FIGS. 1 and 2.

An alternative design of the actuating device 10 is shown in FIG. 6. FIG. 6 shows a side view of the actuating device, viewed from the viewing direction analogous to FIG. 1. The actuating device 10 represented in FIG. 6 also has a cylindrical sleeve 15 and a lower part 16. In contrast to the embodiment illustrated in FIGS. 1 and 2, the lower part 16 has a further section 16a the longitudinal axis of which extends perpendicularly to the longitudinal axis of the lower part 16. The curved spring 17 is secured at the section 16a and at the sleeve 15 at the outside of which the actuating arm 5 is mounted. The lower part 16 in this embodiment is used e.g. for the accommodation of the medicament container of a conventional metered aerosol or inhaler as e.g. a MDI (metered-dose inhaler) which upon actuation dispenses a predetermined amount of a medicament-containing spray mist. The nozzle required for the production of the spray mist is integrated in the lower part 16 or in the section 16a thereof, and the produced spray mist is discharged via the nozzle opening which has the reference numeral 20 in FIG. 6. Thus, said embodiment has the advantage that the nozzle required for the production of a medicament-containing spray mist is already integrated in the actuating device 10. Moreover, it is to be noted that the actuation of the device 10 is effected by pressing together the actuating or atomizer device 10 in the direction of the arrow indicated in FIG. 6. To get the actuating device in FIG. 6 into an operative state, the sleeve must be displaced in the direction of the arrow until the snap hooks 25 lock into the window 26. Thereby the springs 17 are biased, the sleeve 15 is located in the final position and the inner side of the sleeve 17 receives its axial guidance in that it slides on the outside of the cylinder 16, analogous to the guiding elements 19 described in connection with FIGS. 1 and 2.

In order to enable an exact control of the already dispensed doses or of the spraying puffs still available for the patient which makes use of such an inhaler, the above described meter is secured at the actuating device 10 via the bearing pin 8. By pressing together the actuating device 10, i.e. by pressing together of the curved springs 17, the actuating arm 5 is moved which is attached at the sleeve 15 in a suitable manner. Due to the spring effect of the springs 17, the actuating device 10 resumes again its starting position after the pressing together. Apart from said spring effect, the two springs 17 also have a guiding effect with regard to the linear movement of the cylindrical sleeve 15.

Figure 7:
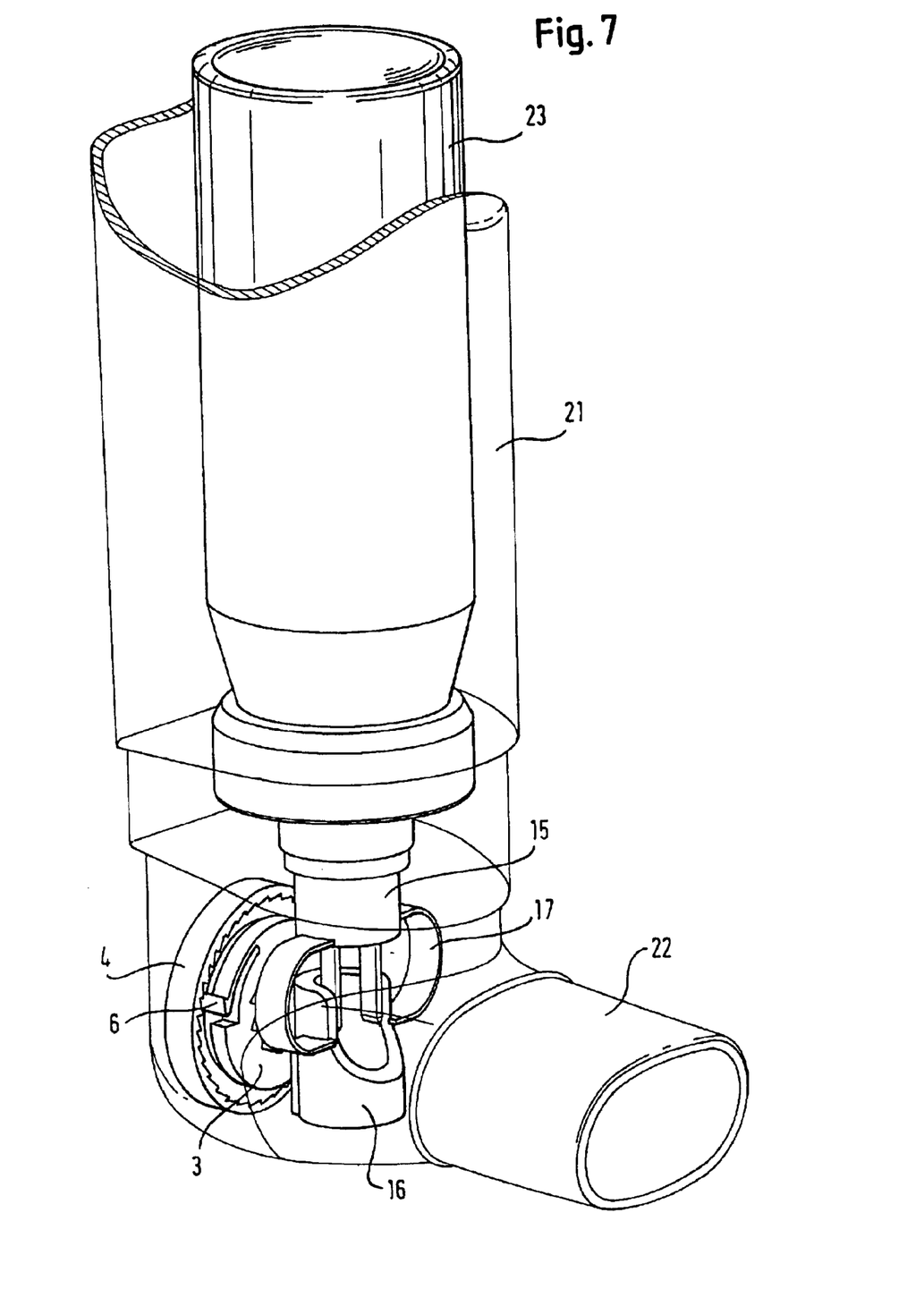
FIG. 7 shows an example of use of the inventive meter in a metering aerosol device.

In FIG. 7 there is illustrated an example of application in which the inventive meter is integrated. FIG. 7 shows a housing 21 of a metering aerosol dispensing device which is provided with a mouthpiece 22. The mouthpiece 22 is arranged at the lower section of the housing 21 in an angular position. In the upper section of the housing 21 there is a metering aerosol container 23 for receiving an aerosol to be atomized. At the lower section of the aerosol container 23 there follows a nozzle section which is inserted into the guiding sleeve 15 of the actuating device 10. The actuating device 10 is connected with the inventive meter consisting of disk units 1, 2, 3 and 4 in order to count and indicate the dispensed or still remaining dosages. During each pumping puff which, as described above, is triggered by the actuation of the actuating device 10, a certain amount of aerosol is dispensed and atomized via a respective nozzle the structure and use of which in such conventional metering aerosol devices is generally known, and can be inhaled by the patient via the mouthpiece 22.

It is advantageous that for the use of an inventive meter in a conventional atomizer or inhaler, this device has not to be changed in its essential components, in particular not the nozzle. By a simple arrangement of an actuating arm for actuating the meter, an easier and simpler structure is rendered possible which can be used universally with already known atomizers and inhalers. Thereby an expensive modification of the already known atomizers can be dispensed with. This is of particular advantage, as for instance in case of a change of the nozzle form such inhalers have to be subjected once again to medical tests for obtaining an approval, which normally are tedious, sumptuous and thus also costly.

What is claimed is:

1. Meter, comprising four disk units (1, 2, 3, 4) which are arranged in parallel to each other, the centers of which are located on an axis extending perpendicularly to the planes of the four disk units (1, 2, 3, 4), and a first disk unit (1) of which has first receiving means (1a) for taking up a force effecting a rotation of the first disk unit around the axis and first transmission means for transmitting the rotation onto a second disk unit (2) which has second receiving means for taking up a force transmitted by the first transmission means and effecting a rotation of the second disk unit (2) around the axis, and a spring cam (6) which is arranged elastically at the outer contour of the second disk unit (2) for the transmission of the rotation onto a fourth disk unit (4) which has an internal toothing (13) for taking up a force transmitted by the spring cam (6, 6a) and effecting a rotation of the fourth disk unit (4) around the axis, wherein at the outer contour of a third disk unit (3) at least one projecting part (11) is provided which in a predetermined rotational position of the second disk unit (2) relative to the third disk unit (3) deviates the spring cam (6) in radial direction, so that the spring cam (6) comes into engagement with the internal toothing (13) of the fourth disk unit (4) and wherein at least one tooth of the internal toothing (13) of the fourth disk unit (4) is filled up in order to lead to a locking effect.

2. Meter, comprising four disk units (1, 2, 3, 4) which are arranged in parallel to each other, the centers of which are located on an axis extending perpendicularly to the planes of the four disk units (1, 2, 3, 4), and a first disk unit (1) of which has first receiving means (1a) for taking up a force effecting a rotation of the first disk unit around the axis and first transmission means for transmitting the rotation onto a second disk unit (2) which has second receiving means for taking up a force transmitted by the first transmission means and effecting a rotation of the second disk unit (2) around the axis, and a spring cam (6) which is arranged elastically at the outer contour of the second disk unit (2) for the transmission of the rotation onto a fourth disk unit (4) which has an internal toothing (13) for taking up a force transmitted by the spring cam (6, 6a) and effecting a rotation of the fourth disk unit (4) around the axis, wherein at the outer contour of a third disk unit (3) at least one projecting part (11) is provided which in a predetermined rotational position of the second disk unit (2) relative to the third disk unit (3) deviates the spring cam (6) in radial direction, so that the spring cam (6) comes into engagement with the internal toothing (13) of the fourth disk unit (4) and wherein at least one tooth of the internal toothing (13) of the fourth disk unit (4) is removed in order to suppress an engagement of the spring cam (6).

3. Meter according to claim 1, characterized in that the spring cam (6) is wedge-shaped and that the width of the spring cam (6) is larger than the thickness of the second disk unit (2) so that the spring cam (6) projects over the second disk unit (2) in the direction of the axis.

4. Meter according to claim 1, characterized in that the third disk unit (3) defines a fixed position and the first, second and fourth disk units (1, 2, 4) are rotatably mounted with respect to the third disk unit (3).

5. Meter according to claim 1, characterized in that the first receiving means of the first disk unit (1) is an external toothing (1a).

6. Meter according to claim 1, characterized in that the first transmission means and the second receiving means are realized in the form of a fixed connection between the first and the second disk unit (1, 2).

7. Meter according to claim 1, characterized in that the fourth disk unit (4) has a second toothing (14) formed circularly around the central point of the fourth disk unit (4) and the third disk unit (3) has a plurality of snap-in toothings (12) for the engagement into the second toothing (14) of the fourth disk unit (4).

8. Meter according to claim 1, characterized in that the radius of the second disk unit (2) is larger than the radius of the first disk unit (1), the radius of the third disk unit (3) is larger than the radius of the first disk unit (1) and smaller than the radius of the second disk unit (2), and the radius of the fourth disk unit (4) is larger than the radius of the first, second and third disk units (1, 2, 3).

9. Meter according to claim 1, characterized in that the four disk units (1, 2, 3, 4) are mounted by means of a bearing pin (8) which has a first section (8b) for slidably mounting the first and second disk unit (1, 2) and a second section (8a) for slidably mounting the fourth disk unit (4), and at which the third disk unit (3) is secured between the first and the second section (8b, 8a).

10. Meter according to claim 9, characterized in that the bearing pin (8) has a third section (8c) for securing the meter which, on the side of the first disk unit (1), extends out of the meter.

11. Meter according to claim 9, characterized in that the second disk unit (2) has an internal toothing (7) and that at the bearing pin (8) there are secured locking elements (9) which interact with the internal toothing (7) of the second disk unit (2).

12. Meter according to claim 1, characterized in that the meter is connected with an actuating device (10).

13. Meter according to claim 12, characterized in that the actuating device (10) includes a sleeve (15) and a lower part (16).

14. Meter according to claim 12, characterized in that at the sleeve (15) an actuating are (5) is attached.

15. Meter according to claim 12, characterized in that the sleeve (15) and the lower part (16) of the actuating device (10) are connected with each other via spring elements (17).

16. Meter according to claim 12, characterized in that at the sleeve (15) there are attached guiding elements (19) in a manner pointing towards the lower part (16).

17. Meter according to claim 12, characterized in that the inner circumferential side of the sleeve (15) slides along the outsides of the guiding elements (19).

18. Meter according to claim 12, characterized in that the lower part (16) has a section (16a) the longitudinal axis of which extends perpendicularly to the longitudinal axis of the lower part (16).

19. Meter according to claim 18, characterized in that the sleeve (15) and the section (16a) are connected with each other via spring elements (17).

20. Meter according to claim 18, characterized in that the sleeve (15) has a window (26) and at the lower part (16) there is attached a snap hook (25) such that the snap hook (25) locks into the window (26) for the axial guidance of the sleeve (15).

21. Use of a meter according to claim 1 in inhalers, atomizers or similar metering aerosol devices.

* * * * *

UNITED STATES PATENT AND TRADEMARK OFFICE
CERTIFICATE OF CORRECTION

PATENT NO. : 6,481,438 B1
DATED : November 19, 2002
INVENTOR(S) : Gallem et al.

It is certified that error appears in the above-identified patent and that said Letters Patent is hereby corrected as shown below:

<u>Title page,</u>
Item [73], Assignee: "PARI GmbH Spezialisten fur Effetive Inhalation," should read
-- PARI GmbH Spezialisten fur effektive Inhalation, --

Signed and Sealed this

Nineteenth Day of August, 2003

JAMES E. ROGAN
*Director of the United States Patent and Trademark Office*